United States Patent [19]
Lopez

[11] Patent Number: 4,831,644
[45] Date of Patent: May 16, 1989

[54] WHEELCHAIR X-RAY RADIOGRAPH APPARATUS AND METHOD

[76] Inventor: Marie A. Lopez, 4801 E. 28th, Tuscon, Ariz. 85711

[21] Appl. No.: 197,048

[22] Filed: May 20, 1988

[51] Int. Cl.[4] .............................................. G03B 42/02
[52] U.S. Cl. ..................................... 378/178; 378/180
[58] Field of Search ........................ 378/178, 177, 180

[56] References Cited

U.S. PATENT DOCUMENTS

| | | |
|---|---|---|
| 3,626,186 | 12/1971 | Allard et al. |
| 3,694,653 | 9/1972 | Allard et al. |
| 3,795,815 | 3/1974 | Weinstock ........................... 378/178 |
| 4,389,057 | 6/1983 | Richard, Jr. |
| 4,572,536 | 2/1986 | Doughty |
| 4,589,124 | 5/1986 | Ruiz |

FOREIGN PATENT DOCUMENTS 2168018A 6/1986 United Kingdom .

OTHER PUBLICATIONS

All-Purpose Cassette Holder, Product brochure, Monee X-Ray Works.

Primary Examiner—Craig E. Church
Attorney, Agent, or Firm—Victor Flores; Harry M. Weiss

[57] ABSTRACT

A wheelchair X-ray radiograph apparatus and method is disclosed for taking a radiograph of a patient in a wheelchair from almost every medically required position. This apparatus includes a modified wheelchair with detachable armrests and backrests, and a radiograph accessory consisting of a radiograph film cassette holder and an opposed brace member attachable to the modified wheelchair utilizing the same mounting used by the detachable armrests and backrests. The apparatus allows the taking of anterior-posterior, posterior-anterior, right and left lateral and skull and cervical spine radiographs of a wheelchair confined patient or trauma patient.

16 Claims, 3 Drawing Sheets

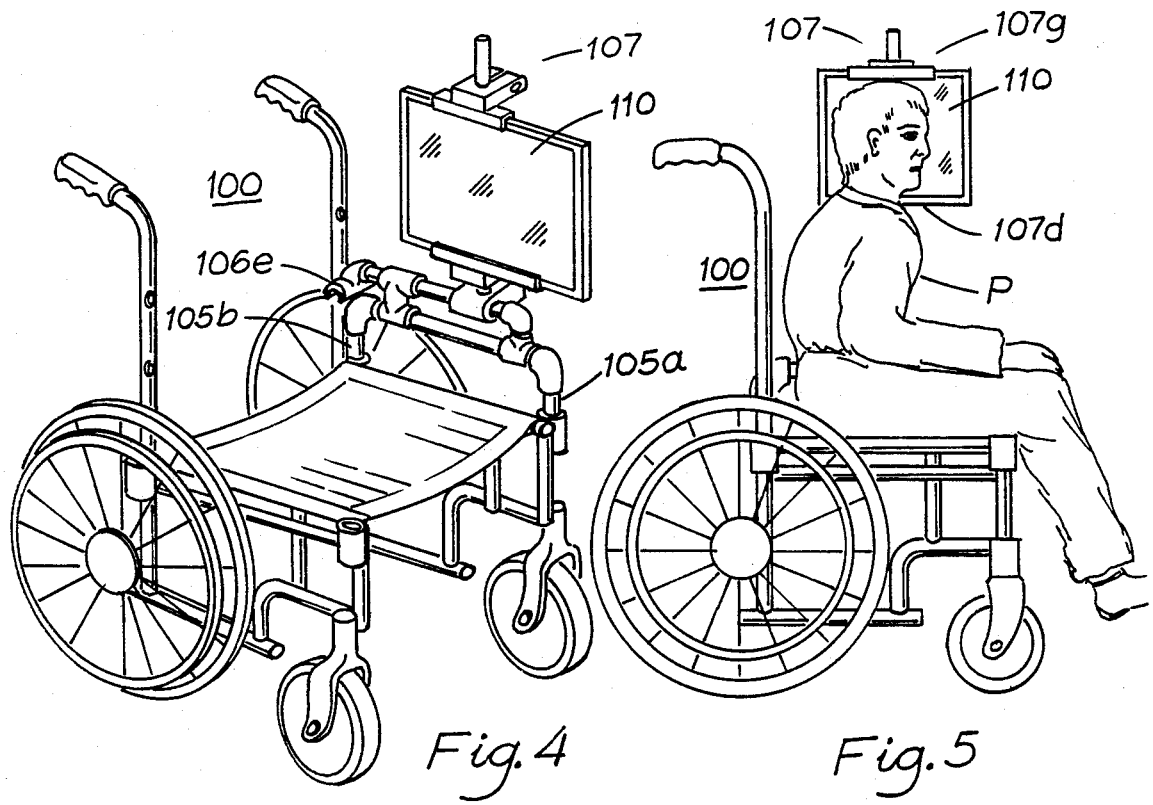
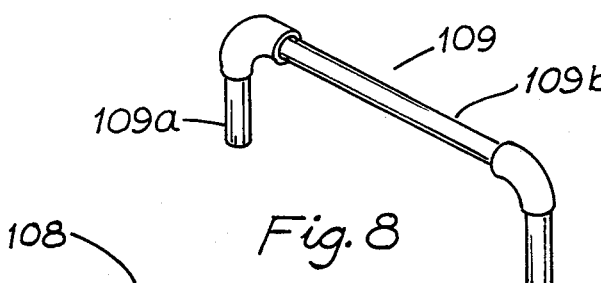
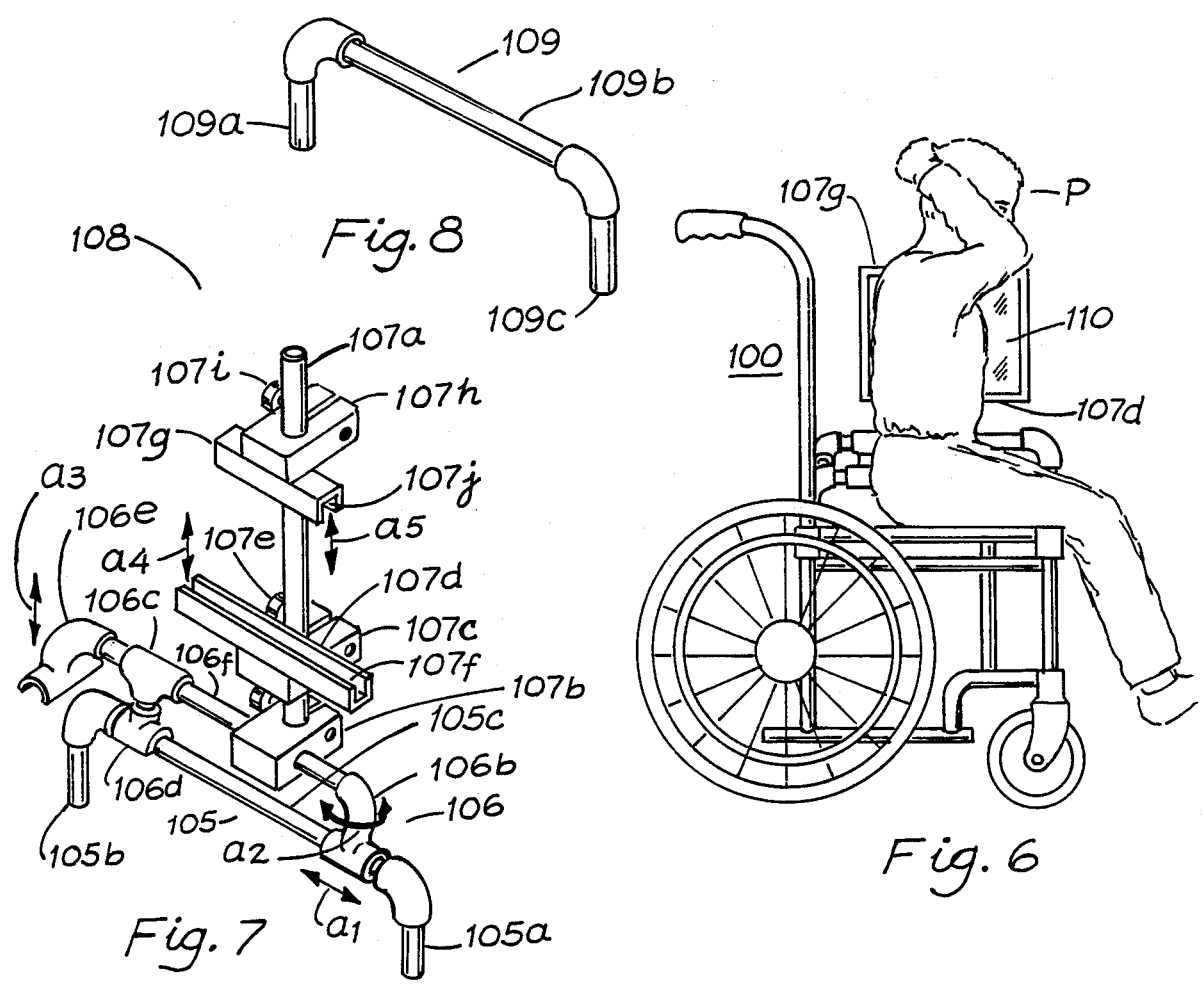
Fig. 4　Fig. 5　Fig. 8　Fig. 7　Fig. 6

WHEELCHAIR X-RAY RADIOGRAPH APPARATUS AND METHOD

FIELD OF THE INVENTION

This invention relates to a new and useful apparatus for taking X-ray radiographs of a patient. More particularly, the invention relates to wheelchair radiograph accessories which are mountable on a modified wheelchair for use in taking X-ray radiographs, hereinafter radiographs, of a patient in a wheelchair in substantially all medically required positions.

DESCRIPTION OF THE PRIOR ART

A major medical problem is encountered by doctors who must take radiographs of non-ambulatory patients. In the past, non-ambulatory patients requiring radiographs were generally transported to a location where radiograph equipment existed and then either transferred to a radiograph table or they were required to stand in front of a wall-mounted radiograph machine. A radiograph lab technician was often required to hold the patient in the proper position. This procedure often subjected the patient to a great deal of discomfort and the radiograph lab technician to a great deal of radiation.

Attempted solutions to this problem have been preferred. U.S. Pat. No. 3,626,186 teaches a wheeled carrier adapted for taking radiographs of a seated patient in various positions including laterals and backs. However, this art teaches no means by which a radiograph can be taken of the back of the patient. Also, the frame of the carrier must be specially constructed and is nothing like the conventional wheelchair used in hospitals today.

U.S. Pat. No. 3,694,653 teaches a film cassette holder to be used with the wheeled carrier referred to above as existing film cassette holders are not suitable or adaptable to this chair. This invention does not teach how a posterior anterior view radiograph may be taken of a patient and requires the special construction of a carrier.

U.S. Pat. No. 4,589,124 teaches a radiograph film holder which is used in taking anterior posterior radiographs of a patient. This invention does not teach how radiographs may be taken of a patient confined to a wheelchair from posterior anterior or lateral positions. Also, the invention does not teach how radiographs may be taken of a confined patient's head.

While the prior art teaches a means for taking radiographs of non-ambulatory patient confined to a wheelchairs, this teaching offers only restricted positions from which the radiographs may be taken or requires that the apparatus be specially manufactured. Therefore, the need exists for a low cost wheelchair radiograph apparatus which allows radiographs to be take from substantially every medically necessary view.

SUMMARY OF THE INVENTION

Accordingly, the primary object of the present invention is to solve these problems and deficiencies in the prior art by providing a wheelchair radiograph apparatus which allows the taking of radiographs from substantially every medically necessary view of a patient seated in a wheelchair. The wheelchair radiograph apparatus includes a modified wheelchair with detachable armrests and backrest, and a wheelchair radiograph accessory consisting of an radiograph film cassette holder means and a brace means attachable to the modified wheelchair. The radiograph film cassette holder is designed to accommodate a plurality of film cassette sizes.

Therefore, to the accomplishments of the foregoing objects, the invention consists of the foregoing features hereinafter fully described and particularly pointed out in the claims, the accompanying drawings and following disclosure describing in detail the invention, such drawings and disclosure illustrating, however, but one of the various ways in which the invention may be practiced.

BRIEF DESCRIPTION OF THE DRAWINGS

FIG. 4 is a perspective view of the wheelchair radiograph accessory shown in FIG. 7 adapted for use in taking left lateral radiographs.

FIG. 5 is a side elevation view of the wheelchair radiograph accessory and wheel chair shown in FIG. 4 adapted for use in taking skull and cervical spine radiographs of the left side of a patient.

FIG. 6 is a side elevation view of the wheelchair radiograph accessory and wheel chair shown in FIG. 4 illustrating use in taking a left lateral radiograph photograph of a patient.

FIG. 7 is a perspective view of the primary component of the wheelchair radiograph accessory in accordance with the present invention, illustrating a lower holder support member, a pivot member and radiograph film cassette holder means.

FIG. 8 is a perspective view of the brace means component of the wheelchair radiograph accessory in accordance with the present invention.

DESCRIPTION OF THE PREFERRED EMBODIMENT

In a more detailed explanation of the invention, reference is now made to the preferred embodiment shown in the figures wherein modified wheelchair 100 is adapted with holder means generally referred to as wheelchair radiograph accessory 108 (FIG. 7) and brace means 109 (FIG. 8).

Figure 1:
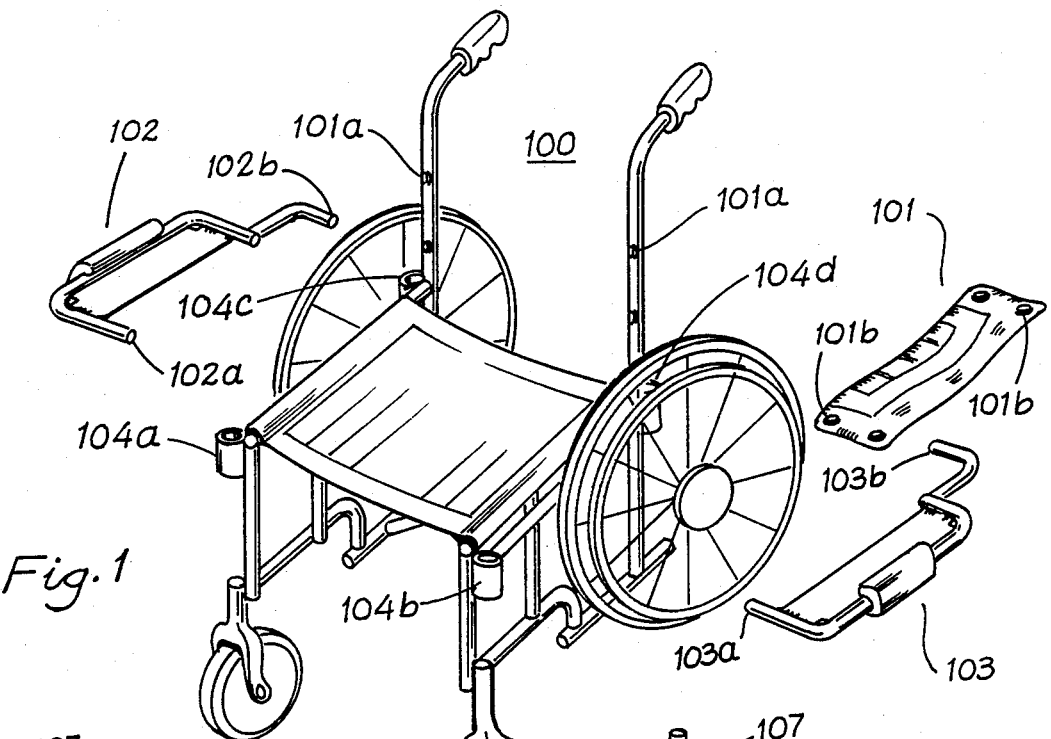
FIG. 1 is a perspective view of the frame of a modified wheelchair illustrating the detachable armrests and backrest.

Referring now to FIG. 1 modified wheelchair 100 comprising a detachable backrest 101, and detachable armrests 102, 103. Detachable backrest 101 attaches to wheelchair 100 by mounting means, shown as snaps 101*b* to buttons 101*a*. Armrests 102 and 103 are attached to modified wheelchair 100 by inserting armrest ends 102a, 102b, 103a, 103b into mounting means 104a, 104c, 104b, 104d, respectively.

The construction of wheelchair radiograph accessory 108 is best understood by reference to FIG. 7. This figure shows that wheelchair radiograph accessory holder means 108 comprises of a lower holder support member 105, a pivot member 106 and an radiograph film cassette holder means 107.

In order that different sizes of film cassette 110 may be readily placed at different elevations, radiograph film cassette holder means 107 is designed having a horizontal adjustment block 107b for sliding on horizontal pivot portion 106f, a lower cassette guide member 107d and upper cassette guide member 107g. In order to obtain vertical adjustment, vertical shaft member 107a is inserted into block 107b and adjusted to the desired position. The tightening mechanism 107k is tightened to hold vertical shaft member 107a in the desired position. To position the film cassette 110, it is inserted in lower cassette guide member slot 107f of lower cassette guide member 107d and is adjusted vertically, per arrow a4, to the desired height. When this height is reached, lower cassette guide member 107d is secured by tightening lower clamp 107c by rotating tightening nut 107e. The top of film cassette 110 is then secured by lowering upper cassette guide member 107g until the top of radiograph film cassette 110 is in upper horizontal slot 107j. Upper clamp 107h is secured by tightening nut 107i.

Figures 2, 3:
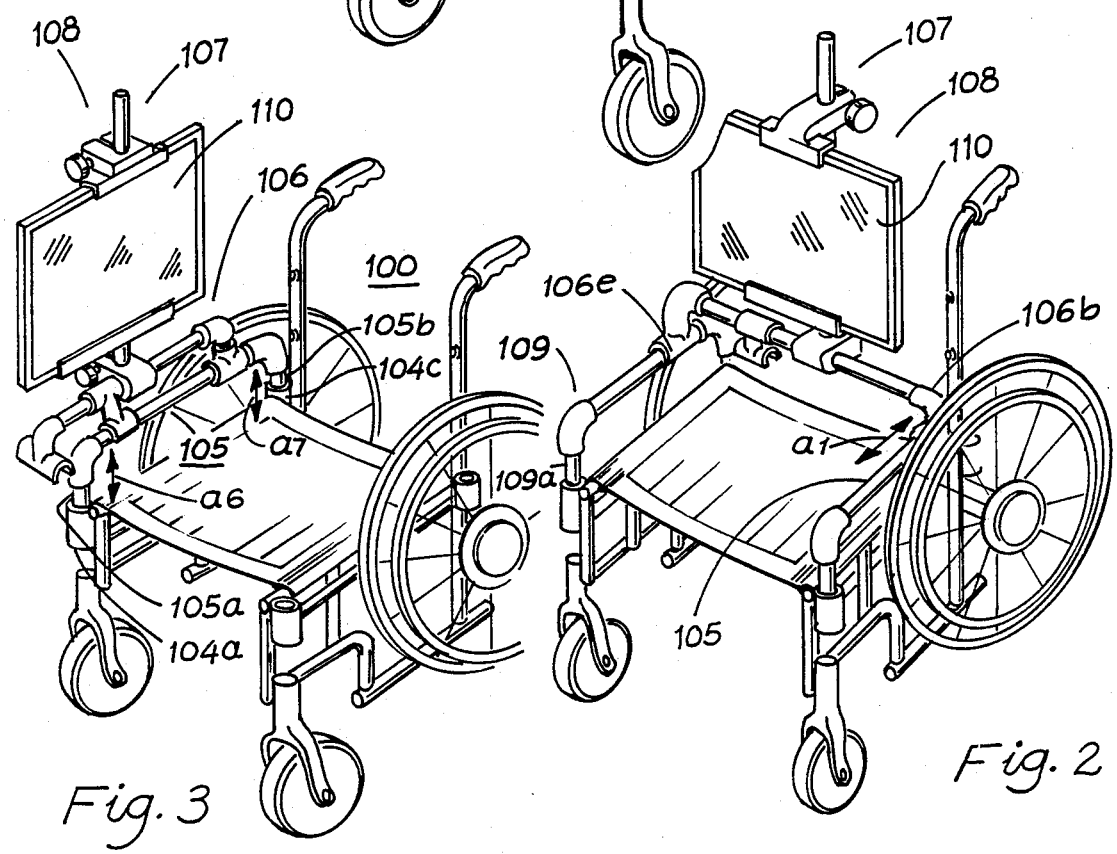
FIG. 2 is a perspective view of the wheelchair radiograph accessory shown in FIGS. 7 and 8 attached to a modified wheelchair in accordance with the present invention and adapted for use in taking anterior-posterior radiographs.
FIG. 3 is a perspective view of the wheelchair radiograph accessory shown in FIG. 7 adapted for use in taking right lateral radiographs.

Wheelchair radiograph accessory holder means 108 becomes functional when used in association with modified wheelchair 100. The flexibility offered by modified wheelchair 100 is enhanced by the articulating features of holder means 108, namely the vertical positioning capability of film cassette holder means 107 discussed above and the rotating capability of pivot member 106 with support aid offered by brace means 109. This combination provides a significant improvement of radiograph methods involving wheelchair confined patients. This combination now allows wheelchair confined patients to be X-rayed, as shown in FIG. 10 and setup in FIG. 9, using radiograph machine 112 by directing an X-ray beam 112a for taking posterior-anterior radiographs, which were not possible with presently available equipment and improves the taking of anterior-posterior radiographs as shown setup in FIG. 2. The combination of the modified wheelchair 100 and holder means 108, alone, greatly improves the taking of radiographs such as a right lateral position as shown in FIG. 3, a left lateral position as shown in FIG. 4 and the skull radiographs, as shown in FIG. 5. A discussion regarding equipment set for taking radiographs from these various positions follows.

In order to take right lateral radiographs of a patient, without requiring the patient to move, the equipment must be setup as shown in FIG. 3. Specifically, lower holder support member 105 is attached to modified wheelchair 100 by inserting vertical mounting member 105b, per arrow a7, into wheelchair receptacle 104c and vertical mounting member 105a into wheelchair receptacle 104a, per arrow a6. Pivot member 106 is rotated per arrow a2, see FIG. 7, until it is parallel to lower holder support member 105 and lowered per arrow a3, see FIG. 7, and secured to lower holder support member bar portion 105c using first snap fitting means 106c and 106d.

In order to take left lateral radiographs of a patient, P, the equipment must be setup as shown in FIG. 4 and illustrated with patient P in FIG. 6. Specifically, lower holder support member 105 is attached to modified wheelchair 100 by inserting vertical mounting member 105a into wheelchair receptacle 104b and vertical mounting member 105b into wheelchair receptacle 104d. This left lateral positioning of holder means 108 is also used for taking skull radiographs as illustrated in FIG. 5. Proper film cassette 110 positioning is achieved in the previously described manner.

In order to take anterior posterior radiographs of a patient P, the equipment is setup as shown in FIG. 2. Specifically, brace means 109 is attached to modified wheelchair 100 by inserting vertical mounting members 109a, 109c into wheelchair receptacles 104a, 104c. The wheelchair radiograph accessory 108 is positioned as if a radiograph was going to be taken from the patient's lateral right side. Pivot member 106 is then rotated counter-clockwise per arrow a2, and slid rearwardly by urging slip means 106b on lower holder support horizontal member 105c, per arrow a1, see FIG. 7, until it is perpendicular to both lower holder support member 105 and brace means 109 at the backrest portion of said modified wheelchair. This will place second snap fitting means 106e above brace means 109 for being secured with horizontal mounting bar 109b. Upper and lower cassette guide members 107d and 107g are then rotated for proper orientation of film cassette 110 until upper and lower horizontal slots 107f, 107j are facing the interior of modified wheelchair 100.

Figure 9:
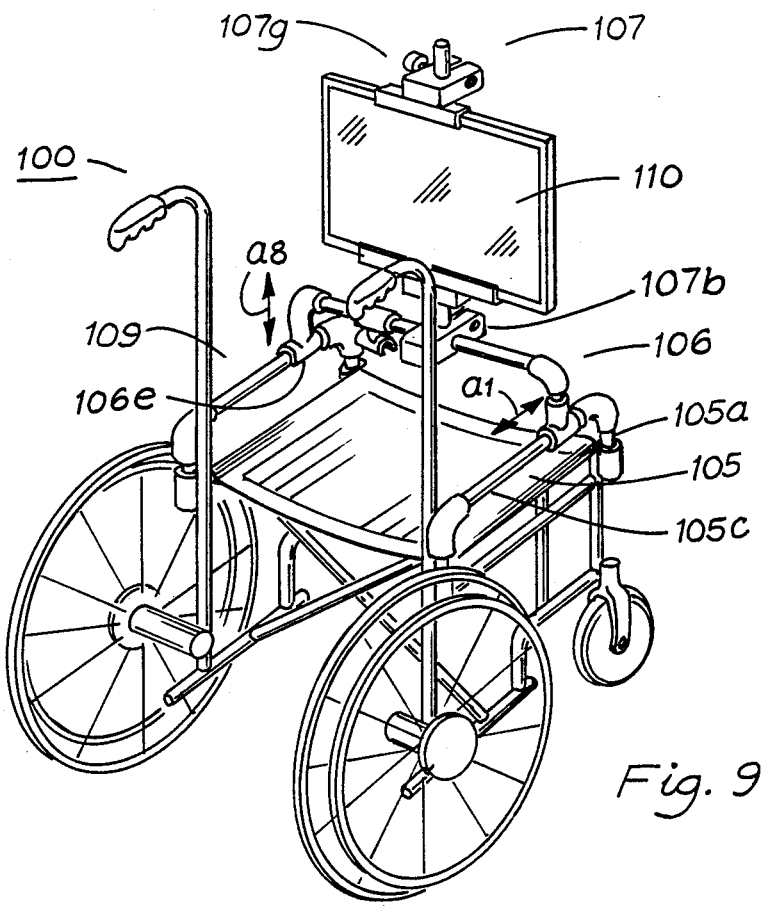
FIG. 9 is a perspective view of a wheelchair radiograph accessory shown in FIG. 7 and 8 attached to a modified wheelchair in accordance with the present invention and adapted for use in taking posterior-anterior radiographs.
Figure 10:
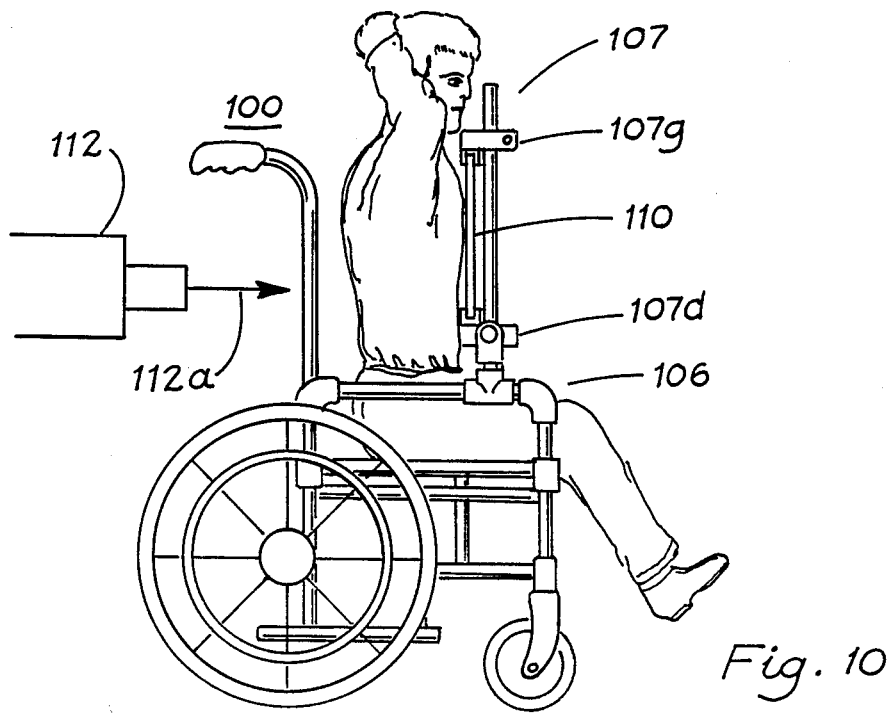
FIG. 10 is a side elevation of the wheelchair radiograph accessory shown in FIG. 9 illustrating use in taking posterior-anterior chest radiogrphs of a patient.

A posterior-anterior radiograph of patient P may be taken by setting up the equipment as shown in FIG. 9 and illustrated in FIG. 10. Specifically, vertical mounting members 109a, 109c of brace means 109 are inserted into wheelchair receptacles 104b, 104d. The wheelchair radiograph accessory holder means 108 is then positioned as if a radiograph was going to be taken from the patient's lateral right side. Pivot member 106 is then rotated counter-clockwise while sliding frontwardly slip means 106b on lower holder support horizontal member 105c until pivot member 106 is perpendicular to the lower holder support means 105 and brace means 109. This will place second snap fitting means 106e above brace means 109 for being secured to horizontal mounting bar 109b. This will place the wheelchair radiograph accessory in front of patient P. Again proper film cassette 110 positioning must be undertaken.

Skull and cervical spine radiographs may be taken from any of the previously described positions by properly positioning the radiograph film cassette holder means 107 according to patient's height, see generally FIG. 5.

Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus.

I claim:

1. A wheelchair radiograph apparatus for taking radiographs of a non-ambulatory patient in every medically required position, said wheelchair radiograph apparatus comprising:
   (a) a modified wheelchair, said modified wheelchair having detachable armrests and a detachable backrest;
   (b) a holder means for supporting a radiograph film cassette, said holder means being detachably secured to said modified wheelchair utilizing mounting means provided on said modified wheelchair for mounting said detachable armrests, said holder means being detachably secured on a left hand side of said modified wheelchair for taking a left lateral radiograph and on a right hand side for taking a right lateral radiograph, said holder means being provided with a pivot member; and (c) a brace means for supporting said pivot member, said brace means being mounted opposite said holder means and being used for supporting said pivot member when positioning said holder means towards the backrest portion of said modified wheelchair for taking an anterior-posterior radiograph and for supporting said pivot member when positioning said holder means toward the front of said wheelchair for taking a posterior-anterior radiograph.

2. A wheelchair radiograph apparatus as recited in claim 1, wherein said modified wheelchair further comprises mounting means for detachably attaching said detachable backrest.

3. A wheelchair radiograph apparatus as recited in claim 1, wherein said holder means further comprises:

(a) a lower holder support member, said lower holder support member being provided with pivoting and sliding attachment means coupled to said pivot member for allowing horizontal rotation and sliding articulation of said pivot member;

(b) a first snap fitting means mounted on said pivot member for coupling to said lower holder support member and thereby supporting said pivot member;

(c) a second snap fitting means mounted at a distal end of said pivot member for coupling to said brace means when said pivot member is positioned orthogonally to said lower holder support member;

(d) a radiograph film cassette holder means attached to said pivot member, said film cassette holder means comprising a lower cassette guide member and an upper cassette guide member, each of said upper and lower cassette guide holders being adapted for vertical sliding on a shaft member to allowing utilization of a variety of radiograph film cassette sizes.

4. A wheelchair radiograph apparatus as recited in claim 3, wherein said mounting means provided on said modified wheelchair for mounting said detachable armrests are mechanically compatible for coupling to a pair of vertical mounting members provided on said lower holder support member and with a similar pair of vertical mounting members provided on brace means.

5. A wheelchair radiograph apparatus as recited in claim 3, wherein:

each of said lower cassette guide member and upper cassette guide member includes a position locking means and a horizontal film guide and support means.

6. A wheelchair radiograph apparatus as recited in claim 4, wherein:

said pivot member supporting said radiograph film cassette holder means being secured to said lower holder support member using said first snap fitting means, and said holder means is mounted on a right hand side of said modified wheelchair for taking right lateral radiographs and on a left hand side of said modified wheelchair for taking left lateral radiographs of said non-ambulatory patient by inserting said pair of vertical mounting members provided on said lower holder support member into, respective sides, said mounting means provided on said modified wheelchair for mounting said detachable armrests.

7. A wheelchair radiograph apparatus as recited in claim 4, wherein:

said holder means being mounted on a right hand side of said modified wheelchair for taking anterior-posterior radiographs and having said pivot member rotated orthogonal to said lower holder support member and being slide rearwardly towards a backrest area of said modified wheelchair, and said brace means being mounted on a left hand side of said modified wheelchair and having said second snap fitting means on said lower holder support member attached to provide support for said holder means.

8. A wheelchair radiograph apparatus as recited in claim 4, wherein:

said holder means being mounted on a left hand side of said modified wheelchair for taking posterior-anterior radiographs and having said pivot member rotated orthogonal to said lower holder support member and being slide frontwardly towards a front seat area of said modified wheelchair, and said brace means being mounted on a right hand side of said modified wheelchair and having said second snap fitting means on said pivot member attached to provide support for said holder means.

9. A wheelchair radiograph apparatus as recited in claim 6, wherein:

said radiograph film cassette holder means is upwardly extendable for taking skull area and cervical spine radiographs.

10. A method of taking radiographs of a non-ambulatory patient in a wheelchair, said method comprising the steps of:

(a) providing a radiology facility having radiograph producing equipment adapted for receiving patients in a wheelchair;

(b) providing a wheelchair radiograph appartus for taking radiographs of a non-ambulatory patient in every medically required position, said apparatus comprising, (i) a modified wheelchair, said modified wheelchair having detachable armrests and a detachable backrest, (ii) a holder means for supporting a radiograph film cassette, said holder means being detachably secured to said modified wheelchair utilizing mounting means provided on said modified wheelchair for mounting said detachable armrests, said holder means being detachably secured on a left hand side of said modified wheelchair for taking a left lateral radiographs and on a right hand side for taking a right lateral radiograph and said holder means being provided with a pivot member, (iii) a brace means for supporting said pivot member, said brace means being mounted opposite said holder means and being used for supporting said pivot member when positioning said holder means towards the backrest portion of said modified wheelchair for taking an anterior-posterior radiograph and for supporting said pivot member when positioning said holder means toward the front of said wheelchair for taking a posterior-anterior radiograph; and (c) detaching from said modified wheelchair said detachable armrests and backrest;

(d) attaching said holder means and said brace means onto said modified wheelchair according to a required radiograph exam;

(e) selecting a proper radiograph film cassette according to said required radiographs exam;

(f) installing said selected radiograph film cassette onto said holder means; and (g) taking said radiographs of said non-ambulatory patient in said modified wheelchair using said provided radiographs equipment.

11. A method of taking radiographs of a non-ambulatory patient in a wheelchair as recited in claim 10, wherein:

said step of attaching includes attaching said holder means and brace means for taking anterior-posterior radiographs.

12. A method of taking radiographs of a non-ambulatory patient in a wheelchair as recited in claim 10, wherein:

said step of attaching includes attaching said holder means and brace means for taking posterior-anterior radiographs.

13. A method of taking radiographs of a non-ambulatory patient in a wheelchair as recited in claim 10, wherein:

said step of attaching includes attaching said holder means for taking right lateral radiographs.

14. A method of taking radiographs of a non-ambulatory patient in a wheelchair as recited in claim 10, wherein:

said step of attaching includes attaching said holder means for taking left lateral radiographs.

15. A method of taking radiographs of a non-ambulatory patient in a wheelchair as recited in claim 10, wherein:

said step of attaching includes attaching said holder means and brace means for taking skull and cervical spine radiographs.

16. A wheelchair radiograph accessory apparatus adapted for mounting onto a modified wheelchair having detachable armrests and backrests and taking radiographs of a non-ambulatory patient in every medically required position, said wheelchair radiograph accessory apparatus comprising:

(a) a holder means for supporting a radiograph film cassette, said holder means being detachably secured to said modified wheelchair utilizing mounted means provided on said modified wheelchair for mounting said detachable armrests, said holder means being detachably secured on a left hand side of said modified wheelchair for taking a left lateral radiograph and on a right hand side for taking a right lateral radiograph, said holder means comprising, a pivot member, a lower holder support member, said lower holder support member being provided with pivoting and sliding attachment means coupled to said pivot member for allowing horizontal rotation and sliding articulation of said pivot member, a first snap fitting means mounted on said pivot member for coupling to said lower holder support member and thereby supporting said pivot member, a second snap fitting means mounted at a distal end of said pivot member for coupling to brace means when said pivot member is positioned orthogonally to said lower holder support member, a radiograph film cassette holder means attached to said pivot member, said film cassette holder means comprising a lower cassette guide member and an upper cassette guide member, each of said upper and lower cassette guide holders being adapted for vertical sliding on a shaft member to allowing utilization of a variety of radiograph film cassette sizes; and (b) a brace means for supporting said pivot member, said brace means being mounted opposite said holder means and being used for supporting said pivot member when positioning said holder means towards a backrest portion of said modified wheelchair for taking an anterior-posterior radiograph and for supporting said pivot member when positioning said holder means toward a front of said wheelchair for taking a posterior-anterior radiograph.

* * * * *